US005744137A

United States Patent [19]

Stone

[11] Patent Number: 5,744,137
[45] Date of Patent: Apr. 28, 1998

[54] OIL EMULSION VACCINES PREPARED WITH ANIMAL, VEGETABLE, AND SYNTHETIC OILS USING A MIXTURE OF NONIONIC SURFACTANTS

[75] Inventor: Henry D. Stone, Winterville, Ga.

[73] Assignee: The United States of America as represented by the Secretary of the Agriculture, Washington, D.C.

[21] Appl. No.: 384,184

[22] Filed: Feb. 6, 1995

[51] Int. Cl.$^6$ .......................... A61K 39/00; A61K 9/66; A61K 7/00; A01N 65/00
[52] U.S. Cl. .......................... 424/184.1; 424/70.17; 424/70.31; 424/214.1; 424/455; 514/937; 514/938; 514/939; 514/943; 520/70; 520/71; 252/174.21; 525/292; 525/323; 525/331.7
[58] Field of Search .................... 252/174.21; 424/214.1, 424/70.11, 70.31, 177, 455, 184.1; 514/937-9, 943; 520/70, 71; 525/292, 323, 331.7

[56] References Cited

U.S. PATENT DOCUMENTS

| | | |
|---|---|---|
| 3,790,665 | 2/1974 | Glass et al. . |
| 3,919,411 | 11/1975 | Glass et al. . |
| 4,024,097 | 5/1977 | Slovinsky et al. . |
| 5,109,026 | 4/1992 | Hoskinson et al. ............ 514/777 |
| 5,122,377 | 6/1992 | Miller et al. . |
| 5,206,316 | 4/1993 | Chuang . |
| 5,376,369 | 12/1994 | Allison et al. . |
| 5,407,899 | 4/1995 | Howell . |
| 5,554,372 | 9/1996 | Hunter . |
| 5,622,649 | 4/1997 | Hunter et al. . |
| 5,650,155 | 7/1997 | Cornelius et al. . |
| 5,656,280 | 8/1997 | Herb et al. . |
| 5,665,383 | 9/1997 | Grinstaff et al. . |
| 5,667,784 | 9/1997 | Cornelius et al. . |

FOREIGN PATENT DOCUMENTS 9511700  5/1995  WIPO .

OTHER PUBLICATIONS

Hunter et al. 1984. J. Immunol. 133(6):3167-3175.
Hunter et al. 1986. Scand. J. Immunol. 23:287-300.
Gordon. 1993. Vaccine. 11(5): 591-593.
Hunter et al. 1991. Vaccine. 9: 250-256.
Brewer et al. 1994. Vaccine. 12(7): 613-619.
Brewer et al. 1992. Immunology 75: 570-75.
Takayama et al. 1991. Vaccine. 9: 257-265.
Hunter et al. 1981. J. Immunology. 127(3): 1244-50.
Bennett et al. 1992. J Immunol. Methods. 153: 31-40.
Edelman et al. 1990. Intern. Rev. Immunol. 7: 51-66.
Bulut et al. 1983. J. Pharm. Pharmacol. 35: 486-488.
Woodard. 1989. Laboratory An. Science. 39(3): 222-25.
Sakaeda et al. 1994. Biol. Pharm. Bull. 17(11): 1490-95.
Avian Diseases 34:979-983, 1990. Stone et al. Efficacy of Experimental Newcastle Disease Water-in-Oil Emulsion Vaccines Formulated from Squalane and Squalene.
Avian Diseases 37:399-405, 1993. Henry D. Stone. Efficacy of Experimental Animal and Vegeble Oil-Emulsion Vaccines for Newcastle Disease and Avian Influenza.
Avian Diseases 37:459-466, 1993. Yamanaka et al. Local Pathological Reactions and Immune Response of Chickens to ISA-70 and Other Adjuvants Containing Newcastle Disease Virus Antigen.
Procedings of the 77th Annual Meeting. U.S. Animal Health Association, 596-600, 1973. Beard et al. A Simple and Rapid Microtest Procedure for Determining Newcastle Hemagglutination-Inhibition (HI) Antibody Titers.
Avian Diseases 27(3):688-697, 1983. Stone et al. Influence of Formulation on the Efficacy of Experimental Oil-Emulsion Newcastle Disease Vaccines.

*Primary Examiner*—Nita Minnifield
*Attorney, Agent, or Firm*—M. Howard Silverstein; John Fado; Gail E. Poulos

[57] ABSTRACT

A composition of a mixture of nonionic surfactants in water-in-oil emulsion vaccines allows the use of animal, vegetable, and synthetic oils as well as mineral oil and pristane. These non-mineral oil vaccines are as efficacious as mineral oil-containing vaccines without the problems associated with the use of mineral oil.

8 Claims, No Drawings

OIL EMULSION VACCINES PREPARED WITH ANIMAL, VEGETABLE, AND SYNTHETIC OILS USING A MIXTURE OF NONIONIC SURFACTANTS

BACKGROUND OF THE INVENTION

1. Field of the Invention

This invention relates to the control of diseases in animals through the use of water-in-oil (w/o) emulsion vaccines using animal, vegetable, and synthetic oils. It relates particularly to the use of oils in w/o vaccines which have rates of efficacy and levels of viscosity comparable to mineral oil w/o vaccines.

2. Description of the Prior Art

Vaccines are used for the prevention of disease in animals. The cornerstone of many infectious disease control programs is induction of specific immunity by vaccination with either live or inactivated microorganisms or their products. Vaccine efficacy depends on many variables, such as the nature and the amount of antigen administered and the presence of adjuvants to enhance immunogenicity. Manipulation of such variables can improve vaccines.

Currently, most if not all vaccines available on the market today contain mineral oil as part of the adjuvant oil phase. In the poultry industry tissue reactions in avian animals injected with mineral oil emulsion vaccines remain a source of poultry condemnations and are of financial concern to the poultry industry. Although the reaction may be due in part to bacterial contamination of the vaccine during use, the mineral oil alone persists for months (Yamamaka et al., Avian Dis. 37:459–466, 1993), may cause undesirable tissue reactions, and is considered to have carcinogenic potential for consumers. To deal with the later concern, a post-vaccination holding period of at least 42 days between vaccination and slaughter has been required for several years (Stone, Avian Diseases 34: 979–983, 1990; Stone, Avian Diseases 37:399–405, 1993, all herein incorporated by reference). Another concern is that accidental injection of operators with mineral oil emulsion is a potential source of liability claims due to personal injury. For these reasons, there is a need for suitable replacements for mineral oil vaccines to be developed. The replacements must have high potency, low viscosity, long shelf life, and minimal tissue reactivity. Also, they must be compatible with mass production techniques, homogenous in appearance, and cost effective.

W/O emulsion vaccines are proven to be more efficacious than vaccines comprised of oil-in-water or aqueous antigen or oil phase alone (Stone, Avian Diseases, 27(3): 688–697, 1993, herein incorporated by reference). Stone et al (Avian Diseases 34: 979–983, 1990) disclose the use of the terpene oils, squalene and squalane, in a vaccine for Newcastle disease in place of mineral oil. They found that the cumulative HI titers using these oils were similar to mineral oil but the viscosity was up to four times greater than those vaccines using mineral oil. Also, the supply source for these terpene oils is limited and more expensive.

Stone (Avian Diseases 37:399–405, 1993) discloses w/o emulsion vaccines using animal and vegetable oils. The vaccines contained an aqueous antigen with an oil phase-to-aqueous phase ratio of 4:1. Emulsification was done with both oil-soluble and water-soluble surfactant added to the oil phase. Beeswax was used as an emulsifier for the non-mineral oil vaccines since the known mineral oil surfactants were not suitable for animal and vegetable oil-containing vaccines. It was reported that the non-mineral oil containing emulsion vaccines had a higher viscosity than mineral oil emulsions of the same relative oil and aqueous components. Low viscosity is an important characteristic for oil emulsion vaccines because it eases the vaccination process, lowering fatigue of working, saving time and work when large numbers of birds are involved. Low viscosity of the oil phase also allows emulsification of a greater amount of aqueous phase for increased volume of antigen or multiple antigens before prohibitive viscosity is reached.

U.S. Pat. No. 5,109,026, to Hoskinson et al., discloses w/o vaccines with mineral oils, squalene, and squalane. The water phase includes a polycationic polyelectrolyte. Emulsifiers such as Arlacel A and Arlacel 80 as oil-soluble emulsifiers or Tween 80 as a water-soluble emulsifier are also used.

The key factor in promoting the efficiency of vegetable and animal oil-containing w/o vaccines is the use of a surfactant(s) with the ability to enhance the immunoactivity of non-mineral oil adjuvants. The accepted standard emulsifying agents for mineral oil vaccines are the Arlacel A, Arlacel 80, and Tween 80. These easily emulsify water phases into mineral oil but do not function in the same capacity with non-mineral oils. Beeswax is suggested as a surface active agent for use with non-mineral vaccines. However, the beeswax-containing emulsion vaccines have viscosities that are much higher than mineral oil vaccines using emulsifying agents such as Arlacel A or 80 and Tween 80 (Stone, Avian Diseases, 37:399–405, 1993).

While various non-mineral oil w/o vaccines have been developed, there remains a need in the art for non-mineral oil w/o vaccines which have rates of efficacy and levels of viscosity comparable with those of mineral oil containing vaccines. The present invention provides a composition for use in non-mineral oil—as well as mineral oil—containing w/o vaccines which is different from prior art compositions and solves some of the problems associated with prior art non-mineral oil w/o vaccines.

SUMMARY OF THE INVENTION

It is therefore an object of the present invention to provide a composition of a mixture of at least two nonionic surfactants for the use in w/o emulsion vaccines.

A further object of the present invention is to provide a composition of a mixture of at least two nonionic surfactants selected from the group consisting of ethoxylated castor oil, propylene glycol laurate, propylene glycol caprylate, and isosteryl diglyceryl succinate.

Another object of the present invention is to provide a composition of a mixture of at least two nonionic surfactants wherein said mixture is made up of equal proportions of each surfactant for use in w/o emulsion vaccines.

Another object of the present invention is to provide a composition of a mixture of at least two nonionic surfactants selected from the group consisting of ethoxylated castor oil, propylene glycol laurate, propylene glycol caprylate, and isosteryl diglyceryl succinate in equal proportions.

A further object of the present invention is to provide a w/o emulsion vaccine containing a composition of a mixture of at least two nonionic surfactants.

Another object of the present invention is to provide a w/o emulsion vaccine containing a composition of a mixture of at least two nonionic surfactants selected from the group consisting of ethoxylated castor oil, propylene glycol laurate, propylene glycol caprylate, and isosteryl diglyceryl succinate.

Another object of the present invention is to provide a w/o emulsion vaccine containing a composition of a mixture of at least two nonionic surfactants wherein said mixture is made up of equal proportions of each surfactant.

Another further object of the present invention is to provide a w/o emulsion vaccine containing a composition of a mixture of nonionic surfactants selected from the group consisting of ethoxylated castor oil, propylene glycol laurate, propylene glycol caprylate, and isosteryl diglyceryl succinate wherein said mixture is made up of equal proportions of each surfactant.

A still further object of the present invention is to provide a method of immunizing animals using a w/o emulsion vaccine containing a composition of a mixture of at least two nonionic surfactants.

Another object of the present invention is to provide a method of immunizing animals using a w/o emulsion vaccine containing a composition of a mixture of nonionic surfactants selected from the group consisting of ethoxylated castor oil, propylene glycol laurate, propylene glycol caprylate, and isosteryl diglyceryl succinate.

A further object of the present invention is to provide a method of immunizing animals using a w/o emulsion vaccine containing a composition of a mixture of at least two nonionic surfactants wherein said mixture is made up of equal proportions of each surfactant.

A still further object of the present invention is to provide a method of immunizing animals using a w/o emulsion vaccine containing a composition of a mixture of nonionic surfactants selected from the group consisting of ethoxylated castor oil, propylene glycol laurate, propylene glycol caprylate, and isosteryl diglyceryl succinate wherein said mixture is made up of equal proportions of each surfactant.

Other objects and advantages of the invention will be readily apparent from the ensuing description.

DETAILED DESCRIPTION OF THE INVENTION

The vaccine formulations of the present invention are applicable to any animal and are especially useful in avian animals, whether domestic or wild, and particularly to those which are commercially reared for meat or egg production. Without limitation thereto, exemplary avians include chickens, turkeys, geese, ducks, pheasants, and the like.

One advantage is the extensive adaptability of the surfactant mixture of the present invention to many oils such that oils homologous to various animals can be used in oil emulsion vaccines such as chicken fat oil in chickens, lard oil in hogs, fish oil in fish, etc., thus reducing the likelihood of extensive tissue reaction. Also, metabolic intermediates such as the medium chain triglyceride oil and propylene glycol derivatives would likely be compatible with many animal species. Furthermore, the surfactant mixture is also useful in mineral oil- and pristane-containing vaccines. The great adaptability of the surfactant mixture for oil-containing vaccines suggests that oils of much lower viscosity than those listed below may be applicable. The viscosity of the nonmineral oil w/o vaccines in the present invention are much lower than that of vegetable, fish, and animal oil vaccines using beeswax surfactant reported in Stone, Avian Diseases, volume 37, pages 399-405, 1993. Another advantage of this invention is in the prevention of lethal diseases such as those which threaten avians without the drawbacks of mineral oil-containing w/o vaccines. Avian diseases include any disease or contamination of viral, bacterial, or other microbial origin. Examples of such, without limitation thereto, include Newcastle disease, avian leukosis, infectious bursal disease, adenovirus disease, reovirus, pox, laryngotracheitis, Salmonella, avian influenza, and Marek's disease.

The term vaccine is defined to mean all types of biological agents used to produce active immunity or competitive exclusion. More particular, the present invention is drawn to w/o emulsion vaccine formulations that are suitable replacements for mineral oil vaccines.

Examples of useful oils include terpene oils such as squalane and squalene; vegetable oils such as soybean oil, olive oil, corn oil, jojoba oil, peanut oil, cottonseed oil, sunflower oil, safflower oil, sesame oil, apricot oil, avocado oil, wheat germ oil, canola oil, linseed oil, and almond oil; fish oils such as shark oil, orange roughy oil, Menhaden oil, and cod liver oil; animal oils such as mink oil, lard oil, and chicken fat oil; and synthetic oils such as ethyl oleate, Miglyol 840 (HULS America Co., 80 Centennial Ave., Piscataway, N.J. 08855-0456), and Captex 300 (Karlshamns Food Ingredients, P.O. Box 569, Columbus, Ohio 43216-0569) as well as mineral oil and pristane.

The surfactants used in the vaccines are a mixture of at least three non-ionic surfactants. The surfactants are mixed in equal proportions volume-to-volume. One example of a mixture of surfactants is Marlowet LVS/K (ethoxylated castor oil, HULS America Company, 80 Centennial Avenue, Piscataway, N.J. 08855-0456, Imwitor 412 (propylene glycol laurate, HULS America Company) and/or Imwitor 408 (propylene glycol caprylate) and Imwitor 780K (isosteryl diglyceryl succinate, HULS America Company) in a ratio of 1:1:1 volume:volume:volume. Imwitor 408 and 412 can be substituted for each other or combined in equal proportions as one component of the surfactant composition. Marlowet LVS may be used alone, however Imwitor 408, 412, and 780K require LVS in pairs or all combined in equal proportions.

The surfactant compounds selected in formulating these vaccines possess fatty acid residues in common with those of natural oils. These formulations promote close molecular packing at the water-oil interface ensuring strength and stability of the emulsion particles. These properties of the emulsion particles are evidenced by excellent vaccine shelf life and in vivo activity. The metabolizability of the several components used favors low tissue reactivity. Concomitantly, the structural strength of the emulsion particles retards the rate of metabolism of the oil phase components by tissue enzymes sufficiently that induction of protective antibody titers ensures. The compatibility of the mixture of surfactants with each other in nonmineral oil vaccines may be due to the fact that each surfactant is of a different stereochemical structure and would not have to compete for exactly the same space around the interface of the oil and emulsified aqueous antigen particle and thus fit together somewhat like a 3-dimensional jigsaw puzzle. This close arrangement would allow more surfactant molecules to participate at the interface for more strength and physical stability.

Oil vaccines are prepared using an oil to aqueous phase (O:A) ratio of approximately about 3 to 5 parts oil phase to approximately about 1 part aqueous phase (volume:volume), a more preferable O:A ratio is approximately about 4:1 (volume:volume). The surfactant mixture is added to the oil phase or to the aqueous phase for approximately 1 minute on a mechanical vortexer at maximum speed. The aqueous phase consists of antigen prepared in PBS or normal allantoic fluid. The antigen can be live or inactivated. The oil phase containing the surfactant composition is added to the aqueous phase containing antigen and is either manually shaken for 15 to 20 seconds or emulsified for 20 seconds using a high-shear probe (Brinkman homogenizer, Brinkman Instruments, Westbury, N.Y.) Polytron 10/35. For large volumes of w/o emulsion vaccines, the aqueous antigen is usually added to the oil phase and dispersed under stir. Oil and surfactant are added to the aqueous phase when small amounts (e.g. 25 ml of vaccine) are made to get smaller aqueous particles. Mineral oil vaccines are prepared as described in Stone et al., Avian diseases, Volume 34, pages 979–983, 1990 and Stone et al., Avian Diseases, Volume 22, pages 666–674, 1978; which are both herein incorporated by reference. Total surfactant volume for vaccines is approximately about 5–25% of the oil phase with a more preferable range of approximately about 10% to about 20% or approximately about 4% to about 20% of the total vaccine volume, with a more preferable range of approximately about 5% to about 16% of the total vaccine volume.

For industrial preparation of the surfactant composition-containing w/o emulsion vaccines, the oil and surfactant-containing aqueous phases are mixed with a Silverson turbine by mixing 5 minutes at 30° C.

The viscosity of the vaccines is recorded as the number of seconds it takes for the meniscus of a vaccine drawn into a 1-ml plastic pipette to descend vertically from the 0.0-ml mark to the 0.4-ml mark at 25° C.

Vaccine efficacy for viral and bacterial antigens is evaluated based on hemagglutination-inhibition (HI) antibody levels in serum. HI antibody levels for viral antigens such as Newcastle disease and avian influenza are determined by the microtest procedure described in Beard et al., Proceedings of the 77th Annual Meeting, U.S. Animal Health Association, 596–600, 1973, which is herein incorporated by reference; using 8 HA units of antigen. Bacterial titers, such as Salmonella enteritidis (SE) titers, are determined by a micro-agglutination test as described in Gast et al., Avian Diseases, vol. 34, 721–728, 1990, which is herein incorporated by reference. Minimum HI titers of 1:40 are indicative of protection against death. The HI tests are conducted on the same day blood samples were drawn.

Gross tissue reactivity is determined following injection of a 0.5-ml dose into muscle tissue. A lesion is considered present if topical observation or incising of muscle tissue at the injection site reveals the tissue to be grossly discolored, demarcated, inflamed, edematous, granulomatous, or indurated, or if tissue appears to contain either encapsulated or diffuse vaccine.

Lesions are deemed severe when an area 3 to 4 cm in diameter is red and inflamed, when superficial and deep muscle is involved, when vaccine exudes from the incised injection site, or when white streaks are visible on the ventral surface of pectoral muscles. Lesions are considered moderate when a 1-to-2-cm-diameter pale-to-red area is involved, when only superficial muscles are involved, when a few drops of vaccine can be scraped from the injection site, and when white streaks on the muscle surface are nearly gone. Lesions are considered light when they contain a pale area with involvement up to 1 cm in diameter, when no vaccine is in the injection site, and when no pale muscle streaks are present.

The following examples illustrate the invention and are not intended to limit the scope of the invention as defined by the claims. A Newcastle disease virus vaccine for chickens is used as a test model system.

EXAMPLE 1

Three-week-old mixed-sex specific-pathogen-free (SPF) white rock chickens are produced by the SPF flock of the USDA, Agricultural Research Services' Southeast Poultry Research Laboratory (SEPRL) and are reared in disease containment buildings. The chickens are free of antibodies against Newcastle disease, avian influenza, infectious bronchitis, mycoplasma infection, Marek's disease, avian encephalomyelitis, lymphoid leukosis, and infectious bursal disease. Chickens are housed in growing batteries in disease containment buildings with filtered air and temperature control (70° F.). Serum samples are collected at 1-week intervals for HI tests between 2 and 7 weeks postvaccination.

EXAMPLE 2

The Ulster strain of Newcastle disease virus (NDV) is harvested in allantoic fluid of 12–13 day embryos infected at 9-days-old. The harvested NDV fluid pool (hemagglutin [HA] titer=1/1600, embryo lethal dose fifty (eld$_{50}$) titers= $10^{9.1}/0.1$ ml) inactivated with 0.1% beta-propiolactone (BPL), preserved with 0.01% thimerosal, and frozen (−70° C.).

Avian influenza (AI) strain A/Turkey/Wisconsin/68 (H5N9) is propagated in the allantois of 9-day-old embryonating chicken eggs by inoculation of approximately $10^3$ fifty percent egg infective doses (EID$_{50}$) of virus. The eggs are incubated for approximately about 48 hours at 37° C. and are chilled to 4° C. before allantoic fluids are harvested. The allantoic fluids contain approximately about $10^{8.9}$ embryo-lethal dose$_{50}$/0.1 ml and have a hemagglutination titer of 1:1600. Inactivation of the fluids for antigen is by treatment with 0.1% beta-propiolactone for 4 hours at approximately about 24° C. The absence of residual infectivity was confirmed by chick embryo inoculation. The antigen is used unconcentrated and is kept at −20° C. until use. No preservatives are added to the preparation.

Salmonella enteritidis (SE) strain SE-E6 is grown up in an overnight culture of tryptic soybroth (TSB) culture. The cultures were set up as three 1.5 liter/flask cultures, each inoculated with approximately about 0.3 ml of loop picked SE from overnight nutrient agar plates. Broths are incubated at approximately about 39° C. overnight. The cultures are centrifuged to pellet the bacteria. The pellets are resuspended in 200 ml phosphate-buffered saline (PBS) and divided into 9 aliquots. Each aliquot is washed twice in PBS and the pelleted bacteria is inactivated with 10 ml of acetone for approximately about 2 hours at room temperature with occasional resuspension. Most of the acetone is removed by pipetting and the remainder is eliminated by evaporation in a desiccator under vacuum. Each tube is equivalent to 500 ml of culture. The SE antigen is kept at −20° C. until use.

EXAMPLE 3

A preliminary study evaluates the use of nonionic surfactants in non-mineral oil w/o emulsion vaccines compared to a mineral oil vaccine. Marlowet LVS/K, Imwitor 408, and Imwitor 780/K are the surfactants tested either alone or as cosurfactants containing 2 or 3 of the surfactants in ratios of 1:1 or 1:1:1 (volume:volume or volume:volume:volume). The oil phase contains soybean oil and Miglyol 840 in a ratio of 1:1, volume:volume. Newcastle disease virus is the antigen. 4 parts of the oil phase containing 10% surfactant is mixed with 1 part aqueous antigen phase. Non-mineral oil vaccines are emulsified using a polytron 10/35 emulsifier at ½ speed for 15 seconds for 25 ml volumes. Groups of 10 chickens per vaccine were tested for serology and vaccine efficacy over 6 weeks. The results are shown below in Table 1.

TABLE 1

Hemagglutination-inhibition (HI) titers induced by NDV water-in oil emulsion vaccines using a mixture of soybean oil (SBO) and Miglyol 840 (840) in a ratio of 1:1 and the nonionic surfactants Marlowet LVS/K (LVS), Imwitor 408 (408), and Imwitor 780/K (780).

| Vaccine Group | Relative viscosity[A] | HI geometric mean titer at weeks post-vaccination[B] 2 | 3 | 4 | 5 | 6 | Cumulative mean titer |
|---|---|---|---|---|---|---|---|
| 10% LVS | 2.8 | 5.5 | 7.6 | 6.5 | 6.4 | 6.3 | 6.5 |
| 10% (LVS:780, 1:1 vol:vol) | 2.2 | 6.1 | 7.8 | 6.6 | 7.4 | 7.2 | 7.0 |
| 10% (LVS:780:408, 1:1:1 vol:vol:vol) | 2.0 | 7.0 | 7.9 | 7.4 | 7.2 | 7.4 | 7.4 |
| Mineral Oil Control | 1.8 | 7.5 | 9.3 | 8.5 | 8.5 | 8.7 | 8.6 |

[A]Number of seconds for the vaccine to drop from the 0.0-ml mark to 0.4-ml mark in a vertical 1-ml plastic pipette.
[B]Reciprocal of HI geometric mean titer based on 10 chickens per group. HI titers are: 5 = 160; 6 = 320; 7 = 640; etc.

The vaccine groups had HI titers that peaked at 3 weeks post vaccination. The vaccine containing mixture of three surfactants had the highest titer as well as a viscosity similar to the mineral oil vaccine.

EXAMPLE 4

To evaluate the potential of various nonmineral oils, 2 ml of the surfactant composition containing ethoxylated castor oil, propylene glycol caprylate, and isosteryl diglyceryl succinate in a 1:1:1 volume:volume:volume ratio is dispersed in 5 ml of antigen using a MaxiMixer II (Thermolyne Corp., Dubuque, Iowa) at maximum speed for 1 minute. 18 mls of oil is added to the antigen-surfactant mixture and manually shaken for 15 to 20 seconds in a 50 ml centrifuge tube. Mechanical emulsification is not used because it causes excess viscosity with some oils. Five chickens per vaccine group receive 0.5 ml of vaccine and are bled for serology over a 5-week period. Nineteen test vaccines and a control mineral oil vaccine were evaluated for efficacy. Separate groups of 5 chickens received 0.5 ml of each vaccine in the breast muscle at 3 weeks of age and were slaughtered 12 days later for examination of the injection site for tissue reactions.

The HI titers are shown below in Table 2.

TABLE 2

Hemagglutination-inhibition (HI) titers induced by NDV water-in-oil emulsion vaccines using various animal, fish, or vegetable oils.

| Vaccine oil and no. | Relative viscosity[A] | Tissue reaction[B] | HI geometric mean titer at weeks post-vaccination[C] 2 | 3 | 4 | 5 | Cumulative mean titer[D] |
|---|---|---|---|---|---|---|---|
| 1. Soybean | 4.1 | L | 6.4 | 6.8 | 6.4 | 6.2 | 6.5[ab] |
| 2. Peanut | 5.0 | M | 6.0 | 7.0 | 7.0 | 7.0 | 6.8[ab] |
| 3. Canola | 4.8 | M | 6.0 | 6.4 | 6.6 | 6.2 | 6.3[b] |
| 4. Corn | 4.2 | L | 6.6 | 7.0 | 6.8 | 6.4 | 6.7[ab] |
| 5. Sunflower | 4.6 | L | 6.2 | 7.0 | 6.8 | 6.6 | 6.7[ab] |
| 6. Jojoba | 4.3 | L | 6.6 | 6.8 | 6.6 | 6.6 | 6.7[ab] |
| 7. Lard | 5.0 | L | 7.2 | 7.8 | 7.4 | 7.2 | 7.4[ab] |
| 8. Sesame Seed | 4.8 | L | 6.8 | 7.0 | 6.6 | 6.4 | 6.7[ab] |
| 9. Cotton Seed | 4.8 | L | 6.6 | 6.6 | 6.8 | 6.6 | 6.7[ab] |
| 10. Menhaden Fish | 3.6 | L | 6.0 | 7.2 | 7.4 | 7.4 | 7.0[ab] |
| 11. Olive | 5.4 | L | 7.2 | 7.4 | 7.0 | 6.4 | 7.0[ab] |
| 12. Squalene | 1.2 | L | 6.6 | 7.0 | 7.4 | 7.4 | 7.1[ab] |
| 13. Squalane | 3.8 | L | 6.2 | 7.2 | 8.0 | 7.2 | 7.2[ab] |
| 14. Chicken Fat | 6.4 | L | 5.0 | 6.2 | 7.4 | 7.4 | 6.5[ab] |
| 15. Wheat Germ | 6.8 | L | 2.6 | 2.8 | 2.8 | 3.0 | 1.4[c] |
| 16. Orange Roughy | 3.0 | L | 7.0 | 7.8 | 7.8 | 8.0 | 7.7[a] |
| 17. Safflower | 4.2 | L | 6.2 | 6.6 | 6.8 | 6.6 | 6.6[ab] |
| 18. Linseed | 4.8 | S | 0.6 | 2.0 | 3.2 | 1.8 | 1.1[c] |
| 19. Almond | 5.0 | L | 6.0 | 6.4 | 6.8 | 7.0 | 6.6[ab] |
| 20. Mineral Oil Control | 2.0 | S | 7.0 | 8.0 | 8.2 | 7.8 | 7.8[a] |

[A]Number of seconds for the vaccine to drop from the 0.0-ml mark to 0.4-ml mark in a vertical 1-ml plastic pipette.
[B]L = light; M = moderate; S = severe TABLE 2-continued Hemagglutination-inhibition (HI) titers induced by NDV water-in-oil emulsion vaccines using various animal, fish, or vegetable oils.

| Vaccine oil and no. | Relative viscosity[A] | Tissue reaction[B] | HI geometric mean titer at weeks post-vaccination[C] | | | | Cumulative mean titer[D] |
|---|---|---|---|---|---|---|---|
| | | | 2 | 3 | 4 | 5 | |

[C]Reciprocal of HI geometric mean titer based on 5 chickens per group. HI titers are: 5 = 160; 6 = 320; 7 = 640; etc.
[D]Means followed by lower-case superscripts are significantly different (P < 0.05) when no superscript letters are in common.

The vaccine groups had HI titers that peaked at 3 weeks or later postvaccination. Except for wheat germ oil, canola oil, and linseed oil, the cumulative mean HI titers for the vegetable oils were not significantly different from that of the mineral oil control group. The fish oil and lard oil groups had the highest HI mean titers but not significantly more than the vegetable oil groups with high titers.

Tissue reactions were severe for mineral oil and linseed oil, moderate for peanut and canola oil, and minor with all other oils.

Viscosity was generally 2.5 to 3.5 times higher in the test oil vaccines than the mineral oil control. Exceptions were squalene oil which was the lowest of all the oils and orange roughy fish oil which was 1.5 times higher than the mineral oil vaccine.

EXAMPLE 5

This example determines the efficacy of soybean oil, medium chain triglyceride oil, and combinations thereof. Soybean oil is selected because of its low cost and availability. Triglyceride oil is selected because of its low viscosity, metabolizable nature, and compatibility with tissue. Non-mineral oil vaccines are emulsified using a polytron 10/35 emulsifier at ½ speed for 15 seconds for 25 ml volumes. Groups of 10 chickens per vaccine were tested for serology over 6 weeks for vaccine efficacy. The results are shown below in Table 3.

TABLE 3

Hemagglutination-inhibition (HI) titers induced by NDV water-oil-oil emulsion vaccines using soybean oil (SBO), Captex medium chain triglyceride (C-300), or combinations thereof.

| Vaccine no. | Oil phase Composition | | Relative viscosity[A] | HI geometric mean titer at weeks post-vaccination[B] | | | | | Cumulative mean titer[C] |
|---|---|---|---|---|---|---|---|---|---|
| | % SBO | % C-300 | | 2 | 3 | 4 | 5 | 6 | |
| 1 | 0 | 100 | 2.0 | 8.3 | 8.3 | 7.9 | 7.7 | 6.8 | 7.8[a] |
| 2 | 20 | 80 | 2.0 | 7.9 | 8.5 | 7.6 | 7.3 | 7.2 | 7.7[a] |
| 3 | 30 | 70 | 2.4 | 7.6 | 8.4 | 7.7 | 7.3 | 7.2 | 7.6[a] |
| 4 | 40 | 60 | 2.7 | 7.2 | 8.1 | 7.9 | 7.7 | 7.2 | 7.6[a] |
| 5 | 50 | 50 | 2.8 | 7.9 | 8.7 | 7.7 | 7.7 | 7.4 | 7.9[a] |
| 6 | 60 | 40 | 3.1 | 7.8 | 8.5 | 8.1 | 7.2 | 7.6 | 8.0[a] |
| 7 | 70 | 30 | 3.5 | 8.2 | 9.0 | 8.4 | 8.0 | 7.8 | 8.3[a] |
| 8 | 80 | 20 | 3.4 | 7.4 | 8.3 | 7.9 | 8.0 | 7.2 | 7.8[a] |
| 9 | 100 | 0 | 3.7 | 7.8 | 7.5 | 8.1 | 7.8 | 7.4 | 7.9[a] |
| 10 | Mineral Oil Control Vaccine | | 1.7 | 7.6 | 9.6 | 9.0 | 8.7 | 7.8 | 8.5[a] |

[A]Number of seconds for the vaccine to drop from the 0.0-ml mark to 0.4-ml mark in a vertical 1-ml plastic pipette.
[B]Reciprocal of HI geometric mean titer based on 10 chickens per group. HI titers are: 5 = 160; 6 = 320; 7 = 640; etc.
[C]Means followed by lower-case superscripts are significantly different (P < 0.05) when they have no common superscript with each other.

As can be seen in Table 3, the mean HI titers of all vaccine groups were similar and less than that of the control mineral oil group, but not significantly. HI titers generally peak at 3 weeks and then slowly decline. Protective HI titers (>1:40) are induced by all vaccines. Viscosity of the mineral oil vaccine was the lowest (1.7) followed by 100% or 80% triglyceride vaccine at 2.0 and soybean oil vaccine at 3.7.

EXAMPLE 6

This example determines the efficacy of soybean oil, propylene glycol dicaprylate/dicaprate and combinations thereof. Propylene glycol dicaprylate/dicaprate oil is chosen because of its low viscosity, emollient qualities, and resistance to "creaming" (stratification of unbroken aqueous phase). Soybean oil is used as a vegetable oil vaccine standard and as a low-cost component of mixed oil vaccines. Test vaccines are emulsified with the Polytron 10/35 in volumes of 25 ml at maximum speed for 20 seconds. Vaccines formulated with either mineral oil, soybean oil, propylene glycol dicaprylate/dicaprate oil or mixtures of soybean oil and propylene diglycol were compared for viscosity and efficacy in groups of 10 chickens over 5 weeks.

The results are shown in Table 4 below.

TABLE 4

Hemagglutination-inhibition (HI) titers induced by NDV water-in-oil emulsion vaccines using soybean oil (SBO), Miglyol diglycol (M-840), or combinations thereof.

| Vaccine no. | Oil phase Composition | | Relative viscosity[A] | HI geometric mean titer at weeks postvaccination[B] | | | | Cumulative mean titer[C] |
|---|---|---|---|---|---|---|---|---|
| | % SBO | % M-840 | | 2 | 3 | 4 | 5 | |
| 1 | 0 | 100 | 0.8 | 7.2 | 7.2 | 6.9 | 6.3 | 7.15[c] |
| 2 | 20 | 80 | 1.2 | 7.4 | 7.1 | 7.4 | 7.2 | 7.28[bc] |
| 3 | 30 | 70 | 1.4 | 8.5 | 7.7 | 7.5 | 7.6 | 7.83[ab] |
| 4 | 40 | 60 | 1.4 | 7.7 | 7.1 | 7.4 | 7.0 | 7.3b[c] |
| 5 | 50 | 50 | 1.7 | 8.4 | 7.7 | 7.9 | 7.5 | 7.9[ab] |
| 6 | 60 | 40 | 2.0 | 8.6 | 7.8 | 7.6 | 7.3 | 7.8[ab] |
| 7 | 70 | 30 | 2.3 | 8.4 | 7.9 | 7.5 | 7.7 | 7.8[ab] |
| 8 | 80 | 20 | 2.8 | 8.2 | 7.8 | 8.0 | 7.7 | 7.9[ab] |
| 9 | 100 | 0 | 4.0 | 7.8 | 7.7 | 7.7 | 7.5 | 7.7[abc] |
| 10 | Mineral Oil Control | | 1.6 | 8.0 | 8.4 | 8.9 | 8.4 | 8.4[a] |

[A]Number of seconds for the vaccine to drop from the 0.0-ml mark to 0.4-ml mark in a vertical 1-ml plastic pipette.
[B]Reciprocal of HI geometric mean titer based on 10 chickens per group. HI titers are: 5 = 160; 6 = 320; 7 = 640; etc.
[C]Means followed by lower-case superscripts are significantly different (P < 0.05) when the superscripts have no letters in common.

oleic acid derivative as an oil likely to be compatible with soybean oil which has collectively over 80% of its fatty acid content in oleic, linoleic, and linolenic acid. Ethyl oleate is selected because of its low viscosity, resistance to "creaming", availability, and low cost. Nonmineral oil vaccines are emulsified mechanically in 25 ml volumes as in Example 6 above. Vaccines formulated with mineral oil, ethyl oleate, soybean oil, and mixtures of ethyl oleate and soybean oil were compared for viscosity and efficacy in groups of 10 chickens over 7 weeks. The results are shown below in Table 5.

TABLE 5

Hemagglutination-inhibition (HI) titers induced by NDV oil-emulsion vaccine using soybean oil (SBO), ethyl oleate, or combinations thereof.

| Vaccine no. | Oil phase composition | | Relative viscosity[A] | HI geometric mean titer at weeks post-vaccination[B] | | | | | Cumulative mean titer[C] |
|---|---|---|---|---|---|---|---|---|---|
| | % SBO | % ethyl oleate | | 2 | 3 | 4 | 5 | 7 | |
| 1 | 0 | 100 | 0.8 | 6.8 | 8.4 | 7.4 | 7.8 | 6.8 | 7.4[a] |
| 2 | 20 | 80 | 1.0 | 7.4 | 8.3 | 8.0 | 7.8 | 6.8 | 7.7[a] |
| 3 | 30 | 70 | 1.2 | 7.3 | 8.5 | 7.9 | 8.0 | 7.6 | 7.9[a] |
| 4 | 40 | 60 | 1.5 | 6.8 | 8.2 | 8.0 | 7.6 | 6.4 | 7.4[a] |
| 5 | 50 | 50 | 1.6 | 7.6 | 8.6 | 8.7 | 7.9 | 7.0 | 8.0[a] |
| 6 | 60 | 40 | 2.0 | 6.8 | 7.4 | 7.4 | 7.8 | 6.8 | 7.2[a] |
| 7 | 70 | 30 | 2.2 | 7.6 | 8.4 | 7.6 | 7.5 | 7.2 | 7.7[a] |
| 8 | 80 | 20 | 2.4 | 7.1 | 7.7 | 7.8 | 7.4 | 6.4 | 7.3[a] |
| 9 | 100 | 0 | 3.8 | 6.6 | 7.9 | 7.6 | 7.4 | 6.8 | 7.3[a] |
| 10 | Mineral Oil Control Vaccine | | 2.0 | 7.3 | 9.1 | 9.5 | 8.7 | 7.8 | 8.5[a] |

[A]Number of seconds for the vaccine to drop from the 0.0-ml mark to 0.4-ml in a vertical 1-ml plastic pipette.
[B]Reciprocal of HI geometric mean titer based on 10 chickens per group. HI titers are 5 = 160; 6 = 320; 7 = 640; etc.
[C]Means followed by lower-case superscripts are significantly different (P < 0.05) when the superscripts have no letters in common.

HI titers of nonmineral oil test vaccinates peaked at 2 weeks and declined slowly to lower levels at 5 weeks. All HI titers are at protective levels. Cumulative mean HI titers of 3 and 5–9 vaccines groups are not significantly different from that of the mineral oil control group and are well above protective levels. Vaccines 1–4 (with up to 40% soybean oil and 60% diglycol) are less viscous than the mineral oil control vaccine. Vaccine No. 1 (100% diglycol oil) had one-half the viscosity of the mineral oil control. Vaccine No. 9 (100% soybean oil) had the highest viscosity with over twice the viscosity of the mineral oil control.

EXAMPLE 7

This example determines the efficacy of soybean oil, ethyl oleate, and combinations thereof in vaccines which need an Cumulative mean HI titers of the vaccine groups were not significantly different from that of the control mineral oil vaccine. Titers generally peaked at 3 weeks and slowly declined by 7 weeks to levels well above protective levels. Vaccines 1–5 (with up to 50% soybean oil) had viscosities equal to or as low as one-half that of the control mineral oil vaccine.

EXAMPLE 8

Different concentrations of the surfactant composition are tested using Captex 300 and Myglyol-840 oils in order to determine working ranges for the surfactant composition. The non-mineral oil vaccines are prepared as in Example 6 above with surfactant concentrations of 2.5%–20% of the oil phase. The oil:aqueous phase ratio is 4:1 as in the above examples. Viscosity and efficacy data are compared over 5 weeks in groups of 10 chickens in each group. The results are shown below in Table 6.

TABLE 6

Effects of Increments of Surfactant Composition in Oil-in-Water Emulsion Vaccine Efficacy

| Percent Surfactant | Relative Viscosity[A] | HI GMT at Weeks Post Vaccination[B] | | | | Mean Cumulative Titer[C] |
|---|---|---|---|---|---|---|
| | | 2 | 3 | 4 | 5 | |
| 2.5 in Captex-300 | 1.2 | 1.5 | 1.3 | 1.4 | 1.1 | 1.3 g |
| 5 | 1.4 | 3.6 | 4.0 | 4.7 | 3.8 | 4.0 f |
| 10 | 1.6 | 5.7 | 6.6 | 6.6 | 6.1 | 6.3 c |
| 15 | 2.0 | 6.1 | 6.9 | 7.1 | 7.1 | 6.8 a |
| 20 | 2.0 | 5.0 | 6.5 | 7.0 | 6.8 | 6.3 b |
| 5 in Myglyol-840 | 0.8 | 4.9 | 5.2 | 5.8 | 5.3 | 5.3 e |
| 10 | 0.8 | 5.5 | 5.8 | 6.2 | 5.8 | 5.3 d |
| 20 | 1.0 | 2.6 | 4.8 | 5.9 | 5.9 | 4.8 e |
| Mineral Oil Control | 1.6 | 6.3 | 7.2 | 7.9 | 7.8 | 7.3 a |

HI titers of 1 = 1:10, 2 = 1:20, 3 = 1:40, 4 = 1:80, 5 = 1:60, 6 = 1:320
Dunnett's method-one way analysis of variance on ranks
[A]Number of seconds for the vaccine to drop from the 0.0-ml mark to 0.4 ml in a vertical 1-ml plastic pipette.
[B]Reciprocal of HI geometric mean titer based on 10 chickens per group. HI titers are 5 = 160; 6 = 320; 7 = 640; etc.
[C]Means followed by lower-case superscripts are significantly different (P < 0.05) when the superscripts have no letters in common.

Table 6 shows that a range of surfactant contents are applicable to two different oils and that optimum amounts for best efficacy are possible. The vaccine group had HI titers that peaked at 4 weeks or later postvaccination. The Captex 300 with 15% surfactant composition in the oil phase had the highest mean HI titer that was not significantly different from the mineral oil control Viscosity was generally less in the two test oil vaccines than the mineral oil control vaccine. Exceptions were the Captex 300 at 15% and 20% surfactant composition in the oil phase which are slightly higher than the mineral oil control vaccine.

EXAMPLE 9

Protective dose fifty ($PD_{50}$) per microliter ($\mu l$) or fraction thereof is determined using 37 test vaccines. $PD_{50}$ values with 95% fiducial limits are calculated by probit analysis and only vaccines which exceed a defined minimum potency value are passed for use (Allan et al., Newcastle Disease Vaccines, Their Production and Use; Food and Agriculture organization of the United Nations, Rome, Page 68, 1987, which is herein incorporated by reference). The oils listed in Table 7 are incorporated into the oil emulsion Newcastle disease vaccines with 10% surfactant composition containing ethoxylated castor oil, propylene glycol caprylate and isosteryl diglyceryl succinate in a 1:1:1 volume:volume:volume ratio. The vaccines are 4 part oil phase to part aqueous antigen phase. 10 chickens per vaccine group received 2.5 µl of each vaccine in the breast muscle at 3 weeks of age. Twenty-one days post vaccination the chickens were challenged with a velogenic Texas strains $10^{5.3}$ $EID_{50}$ (Embryo Infective Dose$_{50}$) by intramuscular route. The birds were observed for 14 days post-challenge. The results are shown below in Table 7.

TABLE 7

Challenge of NDV is $10^{5.3}$ $EID_{50}$ (Embryo Infective Dose$_{50}$) given intramuscularly (IM)
Volume of one dose of vaccine: 0.3 ml = 300 µl
Oil Contents - Cosurfactants not included in percentages

| | $PD_{50}$ per Number of or Fraction of Microliter |
|---|---|
| D1 Soybean Oil 100% (SBO) | D1 = 0.3 = 1000 $PD_{50}$/0.3 ml dose |
| D2 80% SBO + 20% M-840 | D2 = 0.3 |
| D3 80% SBO + 20% Ethyloleate | D3 = 0.5 = 600 $PD_{50}$/0.3 ml dose |
| D4 Miglyol 840 100% | D4 = 1.3 |
| D5 Captex 300 100% | D5 = 2.1 |
| D6 Miglyol 840 100% | D6 = 6.3 = 48 $PD_{50}$/0.3 ml dose |
| D7 Miglyol 810 100% | D7 = 1.1 |
| D8 Miglyol 812 100% | D8 = 0.5 |
| D9 Miglyol 818 100% | D9 = 1.3 |
| D10 Butyloleate 100% | D10 = 1.6 |
| D11 Miglyol 840/Soybean Oil (SBO) | D11 = 0.2 |
| D12 Miglyol 840/Corn Oil 1:1 | D12 = 1.0 |
| D13 Miglyol 840/Lard Oil 1:1 | D13 = 1.0 |
| D14 Miglyol 840/Fish Oil 1:1 | D14 = 0.3 |
| D15 Miglyol 840/Captex 300 1:1 | D15 = 3.8 |
| D16 Ethyloleate/SB Oil 1:1 | D16 = 1.0 |
| D17 Ethyloleate/Corn Oil 1:1 | D17 = 1.0 |
| D19 Ethyloleate/Fish Oil 1:1 | D19 = 1.0 |
| D20 Ethyloleate/Captex 300 1:1 | D20 = 0.6 |
| D21 Ethyl Caprate/Captex 300 1:1 | D21 = 1.0 |
| D22 Ethyl Caprate/Miglyol 840 1:1 | D22 = 10.0 |
| D23 Ethyl Caprate/SB Oil 1:1 | D23 = 2.2 |
| D25 2 pts M-840, 1 pt Corn, 1 pt M-829 | D25 = 0.6 |
| D27 Ethyl Laurate/Lard Oil 1:1 | D27 = 0.6 |
| D28 Ethyl Laurate/M829 1:1 | D28 = 0.6 |
| D30 Ethyl Laurate/Captex 300 1:1 | D30 = 0.3 |
| D31 Ethyl Laurate/Fish Oil | D31 = 0.3 |
| D32 Isopropyl Myristate/-100% | D32 = ≧37.5 |
| D33 Isopropyl Myristate/Fish Oil | D33 = 0.2 |
| D34 Isopropyl Myristate/Lard Oil | D34 = 1.6 |
| D35 Isopropyl Myristate/SB Oil | D35 = 6.0 |
| D36 Isopropyl Myristate/Captex 300 | D36 = 0.34 |
| D37 Isopropyl Myristate/M-840 | D37 = 3.85 |

EXAMPLE 10

The sensitization for maximum secondary Hemagglutination-Inhibition (HI) response was tested with soybean oil w/o emulsion Newcastle disease virus vaccine. Three-week-old white rock chickens, 10 per group, were given aqueous Ulster Newcastle disease virus antigen, prepared as in Example 2, intravenously (50 to 1000 µl) for sensitization. At three weeks post-sensitization, chickens were vaccinated subcutaneously with 0.5 ml of soybean oil w/o emulsion vaccine containing surfactant composition as described in Example 4 above. The results are shown in Table 8 below.

TABLE 8

Sensitization of white rock chickens for maximum secondary Hemagglutination-Inhibition (HI) response with soybean oil water-in-oil emulsion Newcastle disease virus vaccine.

| Group No. | Microliter (µl) Aqueous Antigen | HI-GMT Weeks Post Vaccination (Revaccinate) | | | |
|---|---|---|---|---|---|
| | | 2 | 3 | 4 | 5 |
| 1 | 50 | 0.7 | 0.4 | 5.2 | 8.6 |
| 2 | 100 | 2.4 | 2.0 | 5.8 | 9.6 |

TABLE 8-continued

Sensitization of white rock chickens for maximum secondary Hemagglutination-Inhibition (HI) response with soybean oil water-in-oil emulsion Newcastle disease virus vaccine.

| Group No. | Microliter (μl) Aqueous Antigen | HI-GMT Weeks Post Vaccination (Revaccinate) | | | |
|---|---|---|---|---|---|
| | | 2 | 3 | 4 | 5 |
| 3 | 200 | 3.1 | 2.6 | 5.7 | 9.8 |
| 4 | 300 | 3.4 | 3.1 | 6.5 | 10.1 |
| 5 | 400 | 4.0 | 3.3 | 6.4 | 9.9 |
| 6 | 500 | 3.8 | 3.5 | 6.8 | 10.2 |
| 7 | 600 | 3.7 | 3.1 | 5.7 | 9.9 |
| 8 | 800 | 4.0 | 3.6 | 5.9 | 9.8 |
| 9 | 1000 | 4.1 | 3.7 | 4.7 | 10.2 |
| 10 | 0 | 0.0 | 0.0 | 0.0 | 0.0 |

HI titer of $1 = 1:10$, $2 = 1:20$, $3 = 1:40$, $5 = 1:160$, $7 = 1:640$, $9 = 1:2560$ Table 8 shows that very high (over 9 wells) HI titers are achieved 2 weeks after revaccination from sensitized chickens when a non-mineral oil vaccine (SBO) is used for the secondary dose. Optimum sensitizing dose appears to be 100 ul or greater for this experiment

EXAMPLE 11

The serological response of antigen other than Newcastle disease virus was tested using the non-mineral oil w/o emulsion vaccines. Soybean oil alone or with 20% Captex-300 (C-300) or 20% Myglyol-840 (M-840) was tested as the oil phase which also contains 10% of a surfactant composition. The surfactant composition contains ethoxylated castor oil, propylene glycol laurate or propylene glycol caprylate, and isosteryl diglyceryl succinate in a 1:1:1 volume:volume:volume ratio. The antigen aqueous phase contained avian influenza virus antigen or Salmonella Enteritidis antigen prepared as described in Example 2 above. The vaccines have 4 parts oil phase containing 10% of the surfactant composition and 1 part aqueous antigen and were prepared as described in Example 5 above. Groups of 10 chickens per vaccine were tested for serology over five weeks for vaccine efficacy. The results are shown below in Table 9.

TABLE 9

Serological response of avian influenza (AI) and Salmonella Enteritidis (SE) water-in-oil emulsion vaccines made with Soybean oil (SBO) and mixtures with Captex 300 (C-300) and Miglyol 840 (M-840).

| Vaccine Group | Oil Phase Composition | | | Relative[A] Viscosity | HI Geometric Titer at Weeks Post-Vaccination[B] | | | | Cumulative Mean Titer |
|---|---|---|---|---|---|---|---|---|---|
| | % SBO | % C-300 | % M-840 | | 2 | 3 | 4 | 5 | $\bar{X}$ |
| 1-AI | 100 | 0 | 0 | 3.6 | 4.9 | 6.3 | 6.7 | 6.6 | 6.1 |
| 2-AI | 80 | 20 | 0 | 3.4 | 4.7 | 6.4 | 7.1 | 6.6 | 6.2 |
| 3-AI | 80 | 0 | 20 | 2.8 | 5.0 | 6.8 | 7.0 | 6.7 | 6.4 |
| 4-SE | 100 | 0 | 0 | 4.0 | 6.0 | 5.3 | 5.1 | 5.4 | 5.5 |
| 5-SE | 80 | 0 | 20 | 2.8 | 4.4 | 5.3 | 4.6 | 4.9 | 4.8 |
| 6-AI Mineral Oil Control | | | | 1.6 | 3.8 | 5.6 | 5.8 | 6.8 | 5.8 |
| 7-SE Mineral Oil Control | | | | 2.0 | 5.0 | 5.3 | 6.8 | 4.9 | 5.5 |

[A]Number of seconds for the vaccine to drop from the 0.0-ml mark to 0.4-ml mark in a vertical 1-ml plastic pipette.
[B]Reciprocal of HI geometric mean titer based on 10 chickens per group. HI titers are: $5 = 160$; $6 = 320$; $7 = 640$; etc.

The vaccine groups had HI titers that peaked at 3 weeks or later postvaccination. The cumulative mean HI titers for the non-mineral containing vaccines were not significantly different from that of the mineral oil control groups.

Viscosity was generally higher in the test oil vaccines with the oil composition of 80% soybean oil 20% Miglyol having the lower viscosity.

EXAMPLE 12

The surfactant composition is tested using pristane, mineral oil, soybean oil, M-840, and Captex 300 with a mineral oil control vaccine containing the surfactants Arlarcel 80 and Tween 80 as described in Stone et al., 1978 and 1990, supra in a Newcastle Disease virus vaccine. The vaccines are prepared and evaluated as described in Example 4 above. The results are shown in Table 10 below.

TABLE 10

Hemagglutination-inhibition titers induced by NDV oil-emulsion vaccines using soybean oil (SBO), M-840, Captex 300, mineral oil, and pristane or combinations thereof.

| Vaccine Oil and no. | Relative Viscosity[A] | HI GMT wks postvaccination[B] | | | | |
|---|---|---|---|---|---|---|
| | | 2 | 3 | 4 | 5 | $\bar{X}$ |
| 1. Mineral Oil | 1.6 | 6.3 | 6.9 | 7.8 | 7.9 | 7.2 |
| 2. Pristane | 0.6 | 6.8 | 8.6 | 9.2 | 9.6 | 8.6 |
| 3. SBO | 4.6 | 6.7 | 7.4 | 7.6 | 7.1 | 7.2 |
| 4. M-840 | 0.8 | 5.9 | 6.4 | 6.2 | 5.8 | 6.1 |
| 5. Captex 300 | 1.8 | 6.7 | 7.4 | 6.6 | 6.7 | 6.9 |
| 6. Mineral Oil Ctrl. | 1.8 | 6.6 | 7.7 | 7.7 | 7.2 | 7.2 |

*Vaccines #1–5 are manually emulsified.
*M-840 - Miglyol diglycol
[A]Number of seconds for the vaccine to drop from the 0.0-ml mark to 0.4-ml mark in a vertical 1-ml plastic pipette.
[B]Reciprocal of HI geometric mean titer based on 10 chickens per group. HI titers are: $5 = 160$; $6 = 320$; $7 = 640$; etc.

The vaccine groups have HI titers that peak at 3 weeks or later postvaccination. Mean HI titers are equal to or greater than the mineral oil control vaccine with the exception of M-840. Viscosity was equal to or less than the mineral oil control with the exception of soybean oil.

EXAMPLE 13

18-day-old white leghorn chick embryos are vaccinated in ovo with a Newcastle disease virus vaccine containing the surfactant composition of the present invention using the method of innoculation as described in U.S. patent application Ser. No. 08/269,325 which is herein incorporated by reference. W/O vaccines were prepared with Captex 350 (Karlshamns Food Ingredients Dept., P.O. Box 569, Columbus, Ohio 43216-0569) and Neobee M-5 (Stepan, Food Ingredients Department, 100 West Hunter Avenue, Maywood N.J. 07609), both medium chain triglycerides (MCT) and a mineral oil control. The surfactant composition is equal volumes of ethoxylated castor oil, propylene glycol caprylate, and isosteryl diglyceryl succinate. Vaccines are prepared as described in Example 4 above. The results are shown below in Table 11.

TABLE 11

Hemagglutination-inhibition response of white leghorn chickens vaccinated as 18-day-old embryos with medium chain triglycerides (MCT) and mineral oil Newcastle disease water-in-oil vaccine.

| Vaccine Group | ul Dose | % Hatch[A] | Seroconversion[B] | GM HI Titers of Seroconverters weeks Postvaccination[C] | | | | |
|---|---|---|---|---|---|---|---|---|
| | | | | 2 | 3 | 4 | 5 | $\bar{X}$ |
| 1. Captex 350 MCT | 200 | 96 | 67 | 3.6 | 4.5 | 4.2 | 3.8 | 4.0 |
| 2. Neobee M-5 MCT | 200 | 100 | 80 | 3.2 | 5.1 | 4.2 | 4.0 | 4.1 |
| 3. Mineral Oil Ctrl. | 200 | 80 | 93 | 4.3 | 5.8 | 5.9 | 5.9 | 5.5 |
| 4. No Vaccine | — | 97 | — | <1.0 | <1.0 | <1.0 | <1.0 | <1.0 |

[A]Based on 25 embryos for groups 1, 2, and 3, and 33 embryos for group 4.
[B]Based on 15 embryos vaccinated.
[C]Geometric mean well titers 1 = 1:10, 2 = 1:20, 3 = 1:40, 5 = 1:160, etc.
Notes: Embryos were vaccinated with a 25 gauge needle to 1½ inch depth on the centerline from air cell end toward the small end.

The results show that in ovo vaccination with nonmineral oil-containing w/o vaccines will induce protective HI titers post hatch.

The foregoing detailed description is for the purpose of illustration. Such detail is solely for that purpose and those skilled in the art can make variations therein without departing from the spirit and scope of the invention.

What is claimed is:

1. A water-in-oil emulsion vaccine comprising an adjuvant consisting essentially of
   (a) a mixture of at least two non-ionic surfactants wherein said surfactants are mixed in equal proportions, and
   (b) a water-in-oil emulsion;
   wherein an antigen is directly emulsified into an oil phase of said water-in-oil emulsion.

2. The vaccine of claim 1 wherein said oil is selected from the group consisting of terpene oils, vegetable oils, fish oils, animal oils, synthetic oils, mineral oil, pristane and mixtures thereof.

3. The vaccine of claim 2 wherein said surfactants possess fatty acid residues in common with fatty acid residues on said oils.

4. The vaccine of claim 3 wherein said mixture comprises nonionic surfactants selected from the group consisting of ethoxylated castor oil, propylene glycol laurate, propylene glycol caprylate, and isosteryl diglyceryl succinate.

5. A method for conferring immunity in an animal comprising injecting said animal with a water-in-oil emulsion vaccine containing an adjuvant consisting essentially of
   (a) a mixture of at least two non-ionic surfactants wherein said surfactants are mixed in equal proportions, and
   (b) a water-in-oil emulsion; wherein in an antigen is directly emulsified into an oil phase of said water-in-oil emulsion.

6. The method of claim 5 wherein said oil is selected from the group consisting of terpene oils, vegetable oils, fish oils, animal oils, synthetic oils, mineral oil, pristane and mixtures thereof.

7. The method of claim 6 wherein said surfactants possess fatty acid residues in common with fatty acid residues on said oils.

8. The method of claim 7 wherein said mixture comprises nonionic surfactants selected from the group consisting of ethoxylated castor oil, propylene glycol laurate, propylene glycol caprylate, and isosteryl diglyceryl succinate.

* * * * *